(12) United States Patent
Dunn

(10) Patent No.: US 7,886,906 B1
(45) Date of Patent: Feb. 15, 2011

(54) CATHETER GUIDE WIRE PACKAGING

(76) Inventor: Taryn Dunn, 3210 Gunbarrel Rd., NE., Rushville, OH (US) 43150

( * ) Notice: Subject to any disclaimer, the term of this patent is extended or adjusted under 35 U.S.C. 154(b) by 0 days.

(21) Appl. No.: 12/433,073

(22) Filed: Apr. 30, 2009

(51) Int. Cl.
*B65D 83/10* (2006.01)
(52) U.S. Cl. .................... 206/364; 206/53; 206/438
(58) Field of Classification Search ........... 206/364, 206/53–55, 406, 407, 414, 438; 604/523; 351/97; 24/299; 410/104; 248/447, 595, 248/447.1, 447.2, 450, 456, 457, 458, 462, 248/465.1, 125.7, 407, 628
See application file for complete search history.

(56) References Cited

U.S. PATENT DOCUMENTS

| | | | | |
|---|---|---|---|---|
| 4,707,906 | A | * | 11/1987 | Posey ........................ 29/453 |
| 4,829,999 | A | * | 5/1989 | Auth ........................ 606/1 |
| 5,364,355 | A | * | 11/1994 | Alden et al. ........... 604/103.09 |
| 5,366,444 | A | * | 11/1994 | Martin .................... 604/159 |
| 5,392,918 | A | | 2/1995 | Harrison |
| 5,520,656 | A | | 5/1996 | Byrd |
| 5,709,665 | A | * | 1/1998 | Vergano et al. ............ 604/174 |
| 5,749,370 | A | | 5/1998 | Brooks et al. |
| 5,776,080 | A | | 7/1998 | Thome et al. |
| 6,013,038 | A | | 1/2000 | Pflueger |
| 6,230,372 | B1 | * | 5/2001 | Sokurenko et al. ....... 24/265 CD |
| 6,247,211 | B1 | * | 6/2001 | Bell ......................... 24/306 |
| 6,375,006 | B1 | * | 4/2002 | Samuels ................... 206/364 |
| 6,471,172 | B1 | | 10/2002 | Lemke et al. |
| 6,477,402 | B1 | * | 11/2002 | Lynch et al. ............. 600/434 |
| 6,746,466 | B2 | | 6/2004 | Eidenschink et al. |
| 6,752,800 | B1 | | 6/2004 | Winston et al. |
| 7,104,399 | B2 | | 9/2006 | Duffy et al. |
| 7,172,619 | B2 | | 2/2007 | Richter |
| 7,204,464 | B2 | | 4/2007 | Chandra et al. |
| 2004/0006329 | A1 | | 1/2004 | Scheu |
| 2004/0055926 | A1 | | 3/2004 | Duffy et al. |
| 2004/0059352 | A1 | * | 3/2004 | Burbank et al. ............ 606/148 |
| 2005/0228403 | A1 | * | 10/2005 | Ho et al. .................. 606/113 |
| 2007/0151889 | A1 | | 7/2007 | Brady |
| 2007/0225683 | A1 | * | 9/2007 | Raulerson et al. .......... 604/533 |

\* cited by examiner

*Primary Examiner*—Mickey Yu
*Assistant Examiner*—Jenine M Pagan
(74) *Attorney, Agent, or Firm*—Gold & Rizvi, P.A.; Glenn E. Gold; H. John Rizvi

(57) ABSTRACT

A retainer for maintaining a tubular sheath used to store a catheter guide wire in a coiled configuration includes a body having a bottom defining a plurality of substantially parallel channels. Each channel is designed to closely receive a coil of the tubular sheath. A loop is affixed to and extends adjacently above the body and defines an aperture therethrough for receiving and guiding the catheter guide wire after removal of the guide wire from the tubular sheath.

20 Claims, 5 Drawing Sheets

CATHETER GUIDE WIRE PACKAGING

BACKGROUND OF THE INVENTION

1. Field of the Invention

The present invention relates to medical devices in general and more particularly to packaging for a catheter guide wire.

2. Discussion of the Related Art

Catheters are used in the medical field for a number of purposes. For example in angiographic techniques, a catheter having an inflatable balloon at its distal end is inserted into a patient. In order to accurately position the catheter, a guide wire is first inserted into the patient, often at a remote site such as the femoral artery and the end of the guide wire is moved towards the target site. In order to achieve this, a guide wire is used which is sufficiently rigid to enable it to be pushed along the blood vessels of the patient and yet sufficiently flexible in order to make the necessary turns along its path within the body.

The guide wire is often formed with a curved tip such that the tip may be used to control the path of the distal end of the guide wire. In order to do this, the wire is rotated by the operator. The wire is sufficiently rigid to transmit torque along the length of the wire so as to cause the orientation of the wire, and in particular the orientation of the curved section at the distal end, to rotate in order that the wire can be guided. Once the distal end of the wire is in the target region, a catheter is then slid along the wire in order to carry out whichever medical procedure is involved.

The typical guide wire is from about 135 centimeters to 195 centimeters in length. Since the guide wire is for introduction into a patient's body, the wire must be in a sterile condition as it is brought to area of the medical procedure. Because of its length, the guide wire is often transported in a coiled sterile sheath. However, prior to introduction into the patient, the guide wire must be removed from the sheath. The guide wire, being flexible and of such length, requires a dedicated medical professional such as a nurse to monitor and support the wire to ensure it remains in a sterile condition throughout the procedure.

Thus what is desired is a medical device that is readily sterilized and can be used.

SUMMARY OF THE INVENTION

The present invention is directed to a retainer for use with catheter guide wire packaging such as a coiled tubular sheath that satisfies the need to support a catheter guide wire during a medical procedure and maintain the guide wire in a sterile condition without requiring a dedicated medical professional to perform the task. A retainer for maintaining a tubular sheath used to store a catheter guide wire in a coiled configuration includes a body having a bottom defining a plurality of substantially parallel channels. Each channel is designed to closely receive a coil of the tubular sheath. A loop is affixed to and extends adjacently above the body and defines an aperture therethrough for receiving and guiding the catheter guide wire after removal of the guide wire from the tubular sheath. It is understood the channels can alternately be located on a top of the body.

Another aspect of the present invention is a packaging for a catheter guide wire comprising at least a first retainer having a body with a bottom defining a plurality of parallel channels therein. A loop is affixed to and extends adjacently above the body and further defines an aperture therethrough for receiving and guiding the catheter guide wire after removal of the guide wire from the tubular sheath. A tubular sheath is arranged in a plurality of coils wherein each of the coils is closely received in one of the parallel channels of the first retainer.

Yet another aspect of the present invention is a method of supporting a catheter guide wire during introduction of the guide wire into a patient's body. The method includes placing proximate to a patient, a sterilized catheter guide wire packaging containing a catheter guide wire, wherein the packaging is of the type having a tubular sheath arranged in a coiled configuration, each coil of the sheath received in a channel of first and second diametrically opposed retainers, each retainer including a slotted loop defining an aperture therethrough and further including at least a third retainer having a clamp for clamping to a surgical drape. The packaging is then oriented substantially align the apertures of the loops of the first and second retainers with the site on the patient's body designated for insertion of the catheter guide wire. The packaging is secured to the surgical drape with the clamp of the third retainer. Once the packaging is secured in place, the catheter guide wire is withdrawn from the coiled tubular sheath to an extended uncoiled configuration and then inserted into the loop apertures through the slots defined by the loops. The catheter guide wire is then introduced into the patient.

These and other features, aspects, and advantages of the invention will be further understood and appreciated by those skilled in the art by reference to the following written specification, claims and appended drawings.

BRIEF DESCRIPTION OF THE DRAWINGS

For a fuller understanding of the nature of the present invention, reference should be made to the accompanying drawings in which.

Like reference numerals refer to like parts throughout the several views of the drawings.

DETAILED DESCRIPTION OF THE PREFERRED EMBODIMENT

Figure 1:
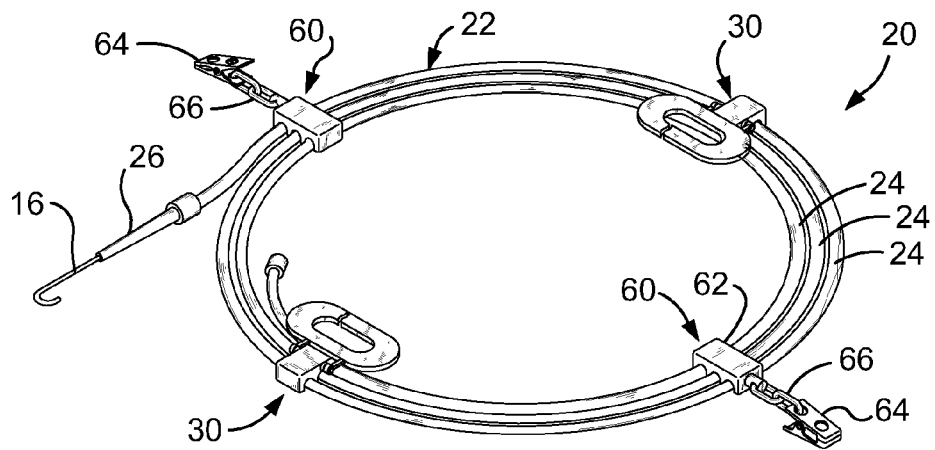
FIG. 1 is a perspective view of a catheter guide wire sheathed in packaging embodying the present invention, wherein the guide loops are in a stowed position.
Figure 4:
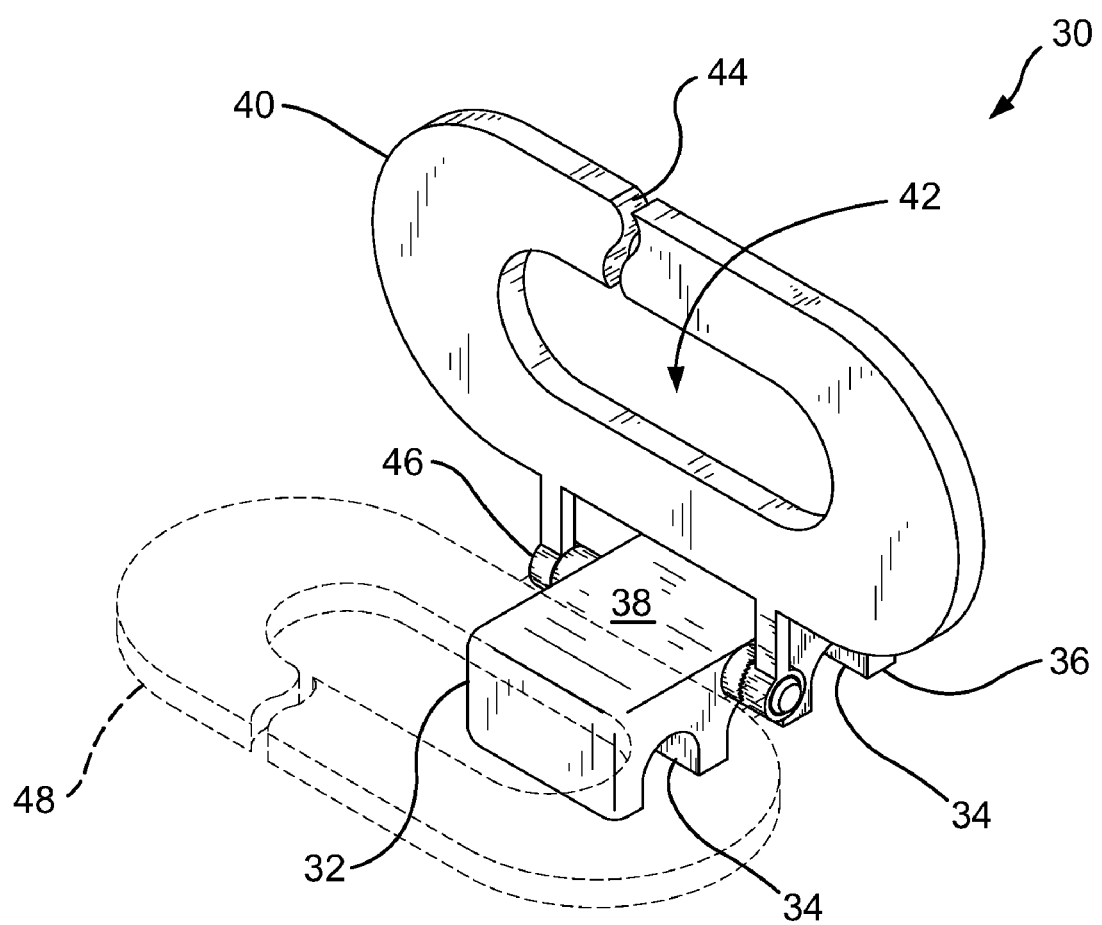
FIG. 4 is an enlarged perspective view of the sheathing retainer and guide loop of FIG. 1.

For purposes of description herein, the terms "upper", "lower", "left", "rear", "right", "front", "vertical", "horizontal", and derivatives thereof shall relate to the invention as oriented in FIGS. 1 and 4. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Turning to the drawings, FIG. 1 shows a packaging 20 for a catheter guide wire 16, which is one of the preferred embodiments of the present invention and illustrates its various components. Packaging 20 has a tubular sheath 22 arranged in a plurality of coils 24 which are secured in a coiled fashion by a plurality of retainers such as first and second retainers 30 and by third and fourth retainers 60. Tubular sheath 22 retains a catheter guide wire 16 within its coiled tubular structure to shield guide wire 16 from contamination and to prevent accidental permanent deformation of guide wire 16 prior to use.

Turning to FIG. 4, retainer 30 has a body 32, which is typically formed from a resilient moldable material. Body 32 has a bottom 36, which defines a plurality of parallel channels 34. It is understood the plurality of parallel channels 34 can be disposed upon a top of the body as an equivalent configuration. Each channel 34 is sized to closely receive and retain therein one of the coils 24 of tubular sheath 22. A loop 40 is affixed to body 32 and positioned adjacent to a top 38 of body 32. Loop 40 can be of any cross sectional configuration such as square, circular, rectangular, or hexagonal and defines an aperture 42. Loop 40 is hinged at 46 with body 32 to permit loop 40 to be selectively raised as illustrated or lowered as illustrated in phantom by 48 to create a lower profile for storage purposes. Loop 40 also defines a slot 44 therethrough. Slot 44 has a width greater than the thickness of guide wire 16 to permit guide wire 16 to be introduced into aperture 42 by translating a mid-portion of guide wire 16 through slot 44 into aperture 42. Slot 44 is preferably non-linear or S-shaped to inhibit guide wire 16 from accidentally disengaging from aperture 42 through slot 44 during introduction of guide wire 16 into a patient. Loop 40 is configured such that in its raised position, aperture 42 is as close to body 32 as possible.

Figure 6:
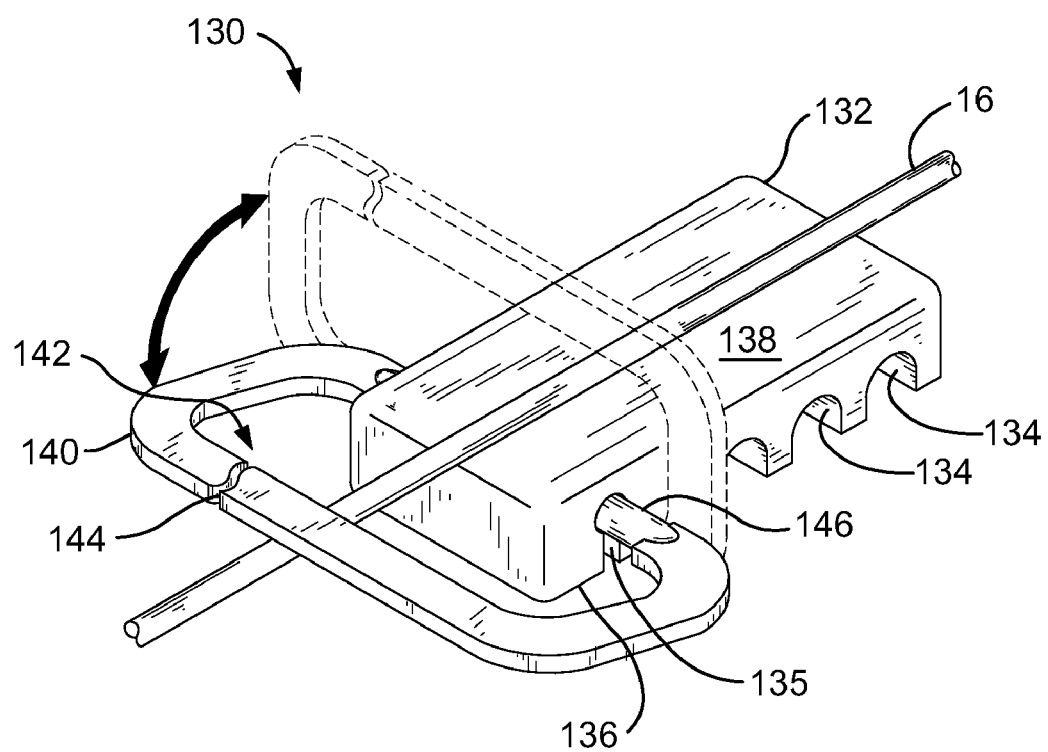
FIG. 6 is an enlarged perspective view of an alternate embodiment sheathing retainer and guide loop.

Turning to FIG. 6, an alternate embodiment retainer 130 is illustrated and can be used in place of retainer 30. Retainer 130 includes a body 132 typically molded of a resilient material. Body 132 has a bottom 136 defining a plurality of parallel channels 134 and 135. It is understood the plurality of parallel channels 134 and 135 can alternately be disposed on a top of the body 132. Channels 134 are sized to accept and closely receive a coil 24 of sheath 22. Channel 135 pivotally receives a portion of loop 140 such that loop 140 can be selectively raised and lowered by rotating loop 140 within channel 135. Loop 140 in combination with top 138 of body 132 defines an aperture 142 therethrough. Loop 140 also defines a slot 144 therethrough. Slot 144 has a width slightly greater than the thickness of guide wire 16 to permit guide wire 16 to be introduced into aperture 142 by translating a mid-portion of guide wire 16 through slot 144 into aperture 142. Slot 144 is preferably non-linear or S-shaped to inhibit guide wire 16 from accidentally disengaging from aperture 142 through slot 144 during introduction of guide wire 16 into a patient.

Retainer 60 generally comprises a body 62 similar to body 32 of retainer 30 wherein body 62 defines a plurality of parallel channels to receive coils 24 of tubular sheath 22. Each retainer 60 includes a clamp 64 flexibly affixed to body 32 such as with a length of chain 66.

Figure 2:
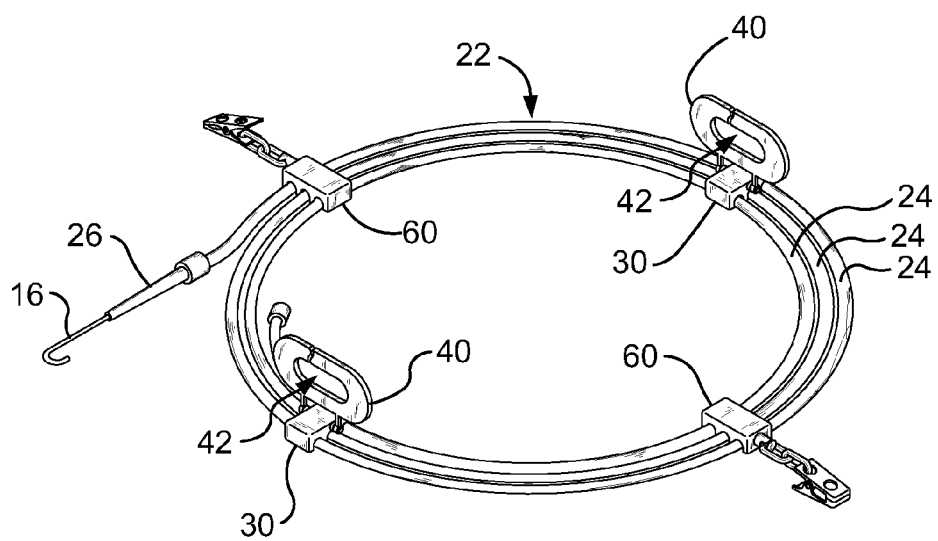
FIG. 2 is a perspective view of a catheter guide wire sheathed in packaging embodying the present invention, wherein the guide loops are in a raised position.

As illustrated in FIGS. 1 and 2, packaging 20 includes first and second retainers 30 securing coils 24 of sheath 22 in their respective channels 34. First and second retainers 30 are oriented in a diametrically opposed manner about the periphery of coiled sheath 22 such that when loops 40 are raised to an upright position, apertures 42 are substantially in alignment one with the other. At least a third retainer 60 and most preferably also a fourth retainer 60 are positioned intermediate to first and second retainers 30 and approximately equidistant thereto such that retainer 30, 60 are positioned at each quadrant of coiled sheath 22.

Figure 3:
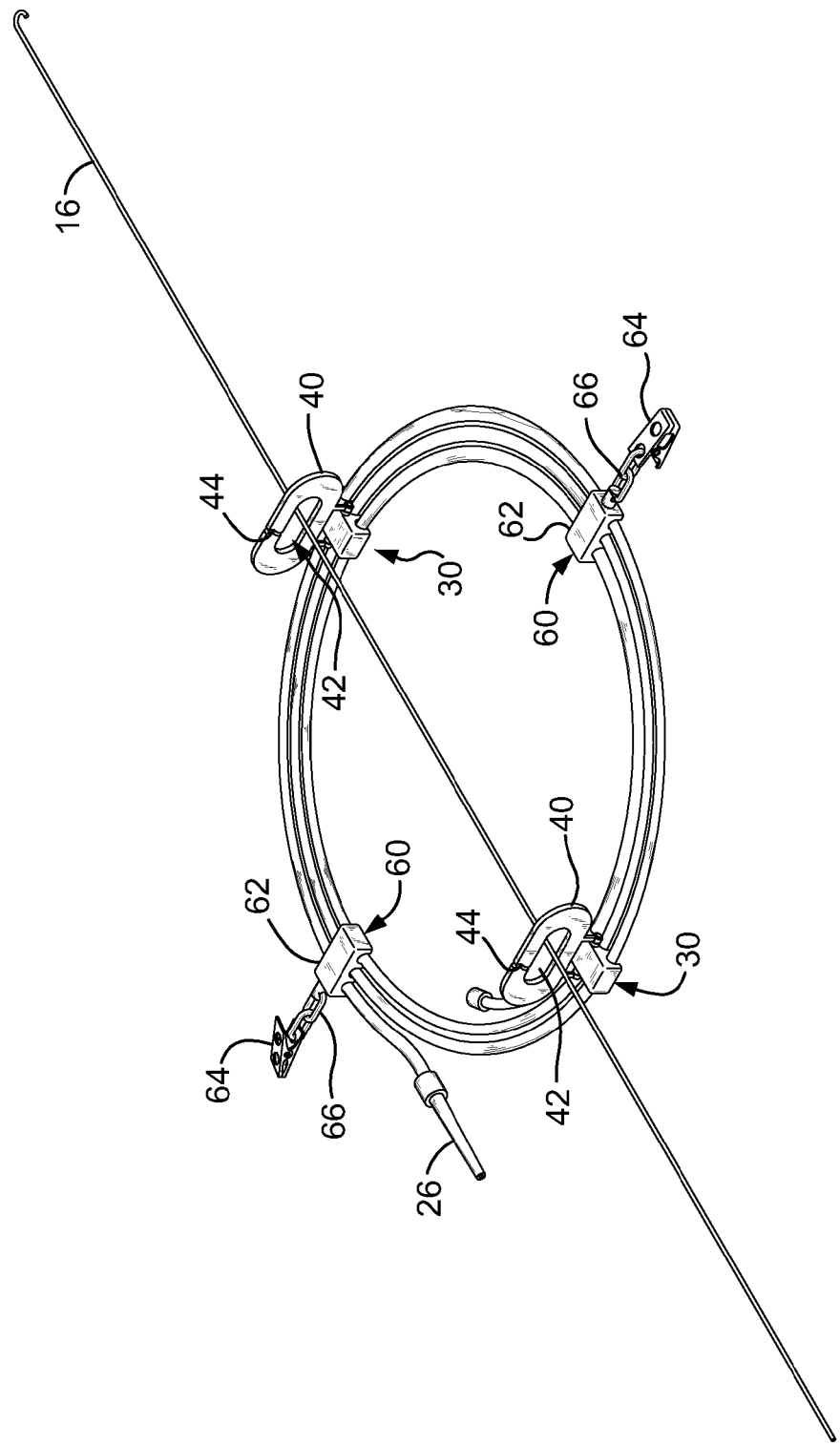
FIG. 3 is a perspective view of the catheter guide wired removed from the tubular sheath and being supported by the guide loops of the packaging.
Figure 5:
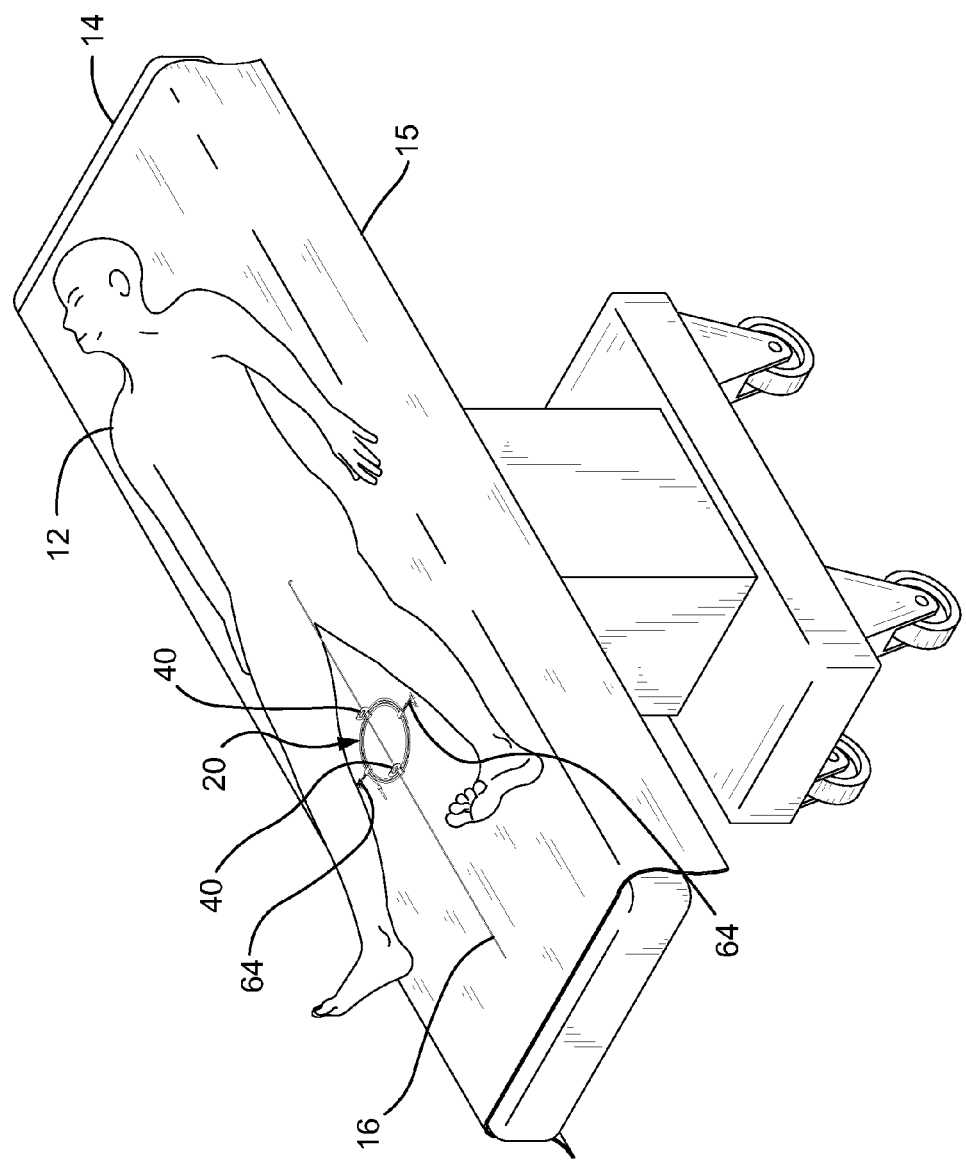
FIG. 5 is a perspective view of a patient undergoing a catheterization wherein the catheter guide wire is being partially supported by the guide loops.

In use, and referring now to FIGS. 3 and 5, packaging 20 is utilized to transport guide wire 16 to the operating theater and to support wire 16 during introduction of the guide wire into the body of patient 12. The sterilized guide wire 16 and packaging 20 is placed proximate to patient 12 in the vicinity of the body site where the catheter is to be introduced. For example, as shown in FIG. 5, guide wire is to be introduced in a femoral vein, thus packaging 20 is placed between the legs of patient 20 on a drape 15 covering operating table 14. Packaging 20 is then oriented to substantially align apertures 44 of loops 44 of first and second retainers 30 with the site on the patient's body designated for introduction of catheter guide wire 16. Packaging 20 is secured to surgical drape 15 with clamps 64 of third and fourth retainers 60. Once packaging 20 is secured in place, catheter guide wire 16 is withdrawn from end 26 of coiled tubular sheath 22 to an extended uncoiled configuration. Guide wire 16 is then inserted into loop apertures 44 by translating a mid-portion of guide wire 16 through slots 44 defined by loops 40. Guide wire 16 is thus supported without requiring a healthcare professional dedicated to the task of supporting guide wire 16. Once guide wire 16 has been inserted into apertures 44, loops 40 can be rotated to a lowered position (such as shown in FIG. 6 with loop 140) to further secure and stabilize guide wire 16 in its orientation with respect to patient 12. Catheter guide wire 16 is then introduced into the patient by the responsible health care professional.

The above description is considered that of the preferred embodiments only. Modifications of the invention will occur to those skilled in the art and to those who make or use the invention. Therefore, it is understood that the embodiments shown in the drawings and described above are merely for illustrative purposes and are not intended to limit the scope of the invention, which is defined by the following claims as interpreted according to the principles of patent law, including the doctrine of equivalents.

I claim:

1. A catheter guide wire storage comprising:
    a tubular sheath formed in a coil;
    a first body and a second body, each body having at least one of a bottom and a top defining a plurality of substantially parallel channels therein, at least one of said channels for closely receiving therein said coil, said coil defining a coil plane;
    a first loop and a second loop, each loop being:
    affixed to and extending adjacently above said respective body, said loop defining an aperture therethrough for receiving and guiding the catheter guide wire after removal of the guide wire from the tubular sheath, said loop defining a loop plane angularly offset from and above said coil plane,
    pivotally assembled to the body, the pivot being designed to maintain the loop plane at an angle offset from the coil plane,
    each body is attached to said coil by said parallel channels, wherein said first body is substantially diametrically opposed to said second body; and
    wherein a guide wire is capable of being stored within the coiled tubular sheath and removed and positioned through said pair of apertures during use.

2. The retainer according to claim 1 wherein said loop defines a slot there-through, said slot having a width slightly greater than a diameter of a catheter guide wire for inserting the catheter guide wire into said aperture.

3. The retainer according to claim 2 wherein said slot is non-linear.

4. The retainer according to claim 3 wherein said slot is S-shaped.

5. The retainer according to claim 1 wherein said loop is pivotally retained in one of said parallel channels.

6. The retainer according to claim 5 wherein said body defines at least a portion of said aperture.

7. The retainer according to claim 6 wherein a portion of said loop not retained by said one parallel channel defines a slot therethrough for inserting the catheter guide wire into said aperture.

8. The retainer according to claim 7 wherein said slot is non-linear.

9. The retainer according to claim 8 wherein said slot is S-shaped.

10. A catheter guide wire storage and surgical assistance device, said device comprising:
- a tubular sheath formed in a coiled configuration, said sheath defining a coil plane;
- a guide wire;
- a first retainer and a second retainer coupled to said tubular sheath, each retainer comprising a body and a loop;
  - said body having at least one of a bottom and a top defining a plurality of coil receiving channels therein; and
  - said loop affixed to and extending adjacently above said body, said loop defining an aperture therethrough for receiving and guiding the catheter guide wire after removal of the guide wire from the tubular sheath, said loop defining a loop plane;
- said first retainer substantially diametrically opposed to said second retainer, wherein each said coil is received in one of said channels of said second retainer;
- wherein said loop plane of each loop is angularly offset from and above said coil plane, and
- wherein the guide wire is capable of being stored within the coiled tubular sheath and removed and positioned through said pair of apertures during use.

11. The catheter guide wire storage and surgical assistance device according to claim 10 wherein said retainer loop is pivotal with respect to said retainer body, wherein the pivot maintains the retainer loop at an angle respective to the retainer body.

12. The catheter guide wire storage and surgical assistance device according to claim 10 wherein each said retainer loop defines a slot therethrough, said slot having a width greater than a diameter of a catheter guide wire for inserting the catheter guide wire into said aperture.

13. The catheter guide wire storage and surgical assistance device according to claim 12 wherein said slot is S-shaped.

14. The catheter guide wire storage and surgical assistance device according to claim 10 wherein said loop of each said retainer is pivotally retained in one of said parallel channels, wherein the pivot maintains the retainer loop at an angle respective to the retainer body.

15. The catheter guide wire storage and surgical assistance device according to claim 14 wherein said retainer body defines at least a portion of said aperture.

16. The catheter guide wire storage and surgical assistance device according to claim 15 wherein a portion of said loop not retained by said one parallel channel defines a slot therethrough for inserting the catheter guide wire into said aperture.

17. The catheter guide wire storage and surgical assistance device according to claim 16 wherein said slot is S-shaped.

18. The catheter guide wire storage and surgical assistance device according to claim 10 further including at least a third retainer, said third retainer comprising:
- a body having a bottom defining a plurality of substantially parallel channels therein, each channel closely receiving therein a coil of said tubular sheath; and
- a clamp flexibly affixed to said body, said clamp for attaching to a surgical drape to secure said packaging in a substantially fixed relationship to a patient.

19. The catheter guide wire storage and surgical assistance device according to claim 18 wherein said clamp is affixed to said body with a chain.

20. A method of supporting a catheter guide wire during introduction of the guide wire into a patient's body, said method comprising the steps of:
- placing proximate to a patient, a sterilized catheter guide wire packaging containing a catheter guide wire, wherein the packaging is of the type having a tubular sheath arranged in a coiled configuration, the coils defining a coil plane, each coil of the sheath received in a channel of first and second diametrically opposed retainers, each retainer including a slotted loop defining an aperture therethrough, the slotted loop defining a loop plane, wherein the loop plane is angled upward from the coil plane, and further including at least a third retainer having a clamp for clamping to a surgical drape;
- orienting the packaging to substantially align the apertures of the loops of the first and second retainers with the site on the patient's body designated for insertion of the catheter guide wire;
- securing the packaging to the surgical drape with the clamp of the at least third retainer;
- withdrawing the catheter guide wire from the coiled tubular sheath to an extended uncoiled configuration;
- inserting the catheter guide wire into the loop apertures through the slots defined by the loops; and
- introducing the catheter guide wire into the patient.

* * * * *